(12) United States Patent
Hon et al.

(10) Patent No.: US 11,185,648 B2
(45) Date of Patent: Nov. 30, 2021

(54) DYNAMIC OUTPUT POWER MANAGEMENT FOR ELECTRONIC SMOKING DEVICE

(71) Applicant: FONTEM HOLDINGS 1 B.V., Amsterdam (NL)

(72) Inventors: Lik Hon, Beijing (CN); Zhuoran Li, Beijing (CN); Fucheng Yu, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 139 days.

(21) Appl. No.: 16/539,783

(22) Filed: Aug. 13, 2019

(65) Prior Publication Data

US 2020/0077705 A1 Mar. 12, 2020

Related U.S. Application Data

(62) Division of application No. 15/538,171, filed as application No. PCT/CN2014/094906 on Dec. 25, 2014, now Pat. No. 10,398,176.

(51) Int. Cl.
*A61M 15/06* (2006.01)
*A61M 11/04* (2006.01)
(Continued)

(52) U.S. Cl.
CPC .............. *A61M 15/06* (2013.01); *A24F 40/50* (2020.01); *A61M 11/042* (2014.02);
(Continued)

(58) Field of Classification Search
CPC ...... A24F 47/002; A24F 47/008; A24F 40/50; A24F 40/53; A24F 42/00; H05B 1/0297; A61M 11/042
(Continued)

(56) References Cited

U.S. PATENT DOCUMENTS 5,505,214 A 4/1996 Collins et al.
9,439,455 B2 9/2016 Alarcon et al.
(Continued)

FOREIGN PATENT DOCUMENTS

CN 201379072 Y 1/2010
CN 102088875 A 6/2011
(Continued)

OTHER PUBLICATIONS

State Intellectual Property Office, Second Office Action for Chinese Application No. 201480084411.1; dated Sep. 24, 2019; 8 pages.
(Continued)

*Primary Examiner* — Hae Moon Hyeon
(74) *Attorney, Agent, or Firm* — Perkins Coie LLP; Kenneth H. Ohriner

(57) ABSTRACT

A dynamic output power management unit for a heating circuit of an electronic smoking device is disclosed, the heating circuit having a heating element connected to a power source via a first switching element, the unit having at least one voltage detection device to detect voltage values at various points of the heating circuit; and a controller configured to deriving a resistance of the heating element, estimating a discharge time or a power consumption value of the power source such that an energy converted in a period of time is substantially identical to a predetermined energy conversion value for a same period of time.

14 Claims, 12 Drawing Sheets

(51) Int. Cl.
*A24F 40/50* (2020.01)
*H05B 1/02* (2006.01)
*A24F 40/10* (2020.01)

(52) U.S. Cl.
CPC ............ *H05B 1/0297* (2013.01); *A24F 40/10* (2020.01); *A61M 2205/3317* (2013.01); *A61M 2205/702* (2013.01); *A61M 2205/8206* (2013.01); *A61M 2205/8212* (2013.01); *A61M 2205/8237* (2013.01)

(58) Field of Classification Search
USPC .................................................. 131/328, 329
See application file for complete search history.

(56) References Cited

U.S. PATENT DOCUMENTS

| | | | |
|---|---|---|---|
| 10,111,465 | B2 * | 10/2018 | Liu ...................... A24F 40/57 |
| 2012/0111347 | A1 | 5/2012 | Hon |
| 2013/0104916 | A1 | 5/2013 | Bellinger et al. |
| 2013/0319440 | A1 * | 12/2013 | Capuano ............... A61M 15/06 131/329 |
| 2014/0270727 | A1 | 9/2014 | Ampolini et al. |
| 2014/0278250 | A1 * | 9/2014 | Smith .................. A24F 47/002 702/187 |
| 2014/0334804 | A1 | 11/2014 | Choi |
| 2015/0173124 | A1 | 6/2015 | Qui |
| 2016/0050974 | A1 | 2/2016 | Galloway et al. |
| 2016/0278431 | A1 | 9/2016 | Liu |
| 2016/0316822 | A1 | 11/2016 | Liu |
| 2016/0374392 | A1 | 12/2016 | Liu |
| 2017/0238596 | A1 * | 8/2017 | Matsumoto ............ A61K 9/007 |
| 2018/0043114 | A1 | 2/2018 | Bowen et al. |

FOREIGN PATENT DOCUMENTS

| | | |
|---|---|---|
| CN | 102940313 A | 2/2013 |
| CN | 202749479 U | 2/2013 |
| CN | 103889258 A | 6/2014 |
| CN | 104114049 A | 10/2014 |
| CN | 104116138 A | 10/2014 |
| DE | 202013010986 U1 | 2/2014 |
| EP | 2143346 A1 | 1/2010 |
| WO | 2013060781 A1 | 5/2013 |
| WO | 2014075369 A1 | 5/2014 |
| WO | 2014150247 A1 | 9/2014 |

OTHER PUBLICATIONS

United Kingdom Intellectual Property Office, Combined Search and Examination Report, Application No. GB 1502497.9, dated Mar. 30, 2015.
Patent Cooperation Treaty, International Search Report and Written Opinion, Application No. PCT/CN2014/094906, dated Oct. 8, 2015.
European Patent Office, extended European Search Report for Application No. 14908768.6; dated Nov. 21, 2018; 8 pages.
State Intellectual Property Office, First Office Action for Chinese Application No. 201480084411.1; dated Mar. 29, 2019; 12 pages.

* cited by examiner

DYNAMIC OUTPUT POWER MANAGEMENT FOR ELECTRONIC SMOKING DEVICE

RELATED APPLICATION

This application is a divisional of U.S. Application Ser. No. 15/538,171, filed Jun. 20, 2017, now pending and titled Dynamic Output Power Management for Electronic Smoking Device which is a U.S. National Phase Application of International Patent Application No. PCT/CN2014/094906, filed Dec. 25, 2014, both incorporated herein by reference.

TECHNICAL FIELD

The present invention relates to an output power management unit (PMU) For electronic smoking devices.

BACKGROUND OF THE INVENTION

An electronic smoking device, such as an electronic cigarette, usually has a heating element for vaporizing liquid and a power supply for providing power to the heating element. In some cases, the heating element can be a component of an atomizer. Providing a consistent energy supply to the heating element improves the consistency of each puff. Each puff on average takes about the same time (e.g. 2.5 seconds/puff). A consistent energy supply to the heating element for each puff may be achieved via consistent power output of the power supply during this interval.

Typically, the power supply is a disposable or rechargeable battery with working voltage decreasing over its useful life. The decreasing voltage may result in inconsistent puffs. Moreover, the heating elements may have resistances that vary in operation due to factors, such as the amount of e-solution, the heating element contacts, and the operating temperature.

Therefore, there is a need for a dynamic output power management unit to provide a stable output power in response to the changing capacity of the battery, and/or the changing resistance of the heating element.

DETAILED DESCRIPTION

Figure 1:
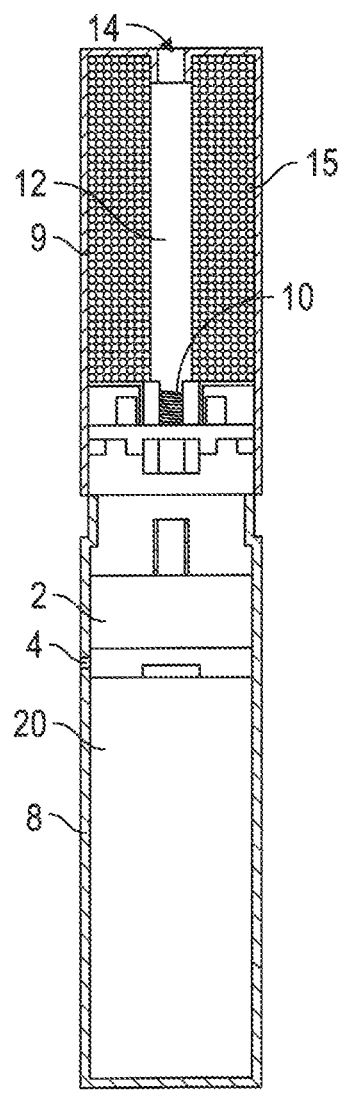
FIG. 1 is a schematic drawing of an electronic cigarette or similar vaporizing device.

A dynamic output power management unit for an electronic cigarette, cigar pipe etc. Provides a substantially constant amount of vaporized liquid in a predetermined time interval, for example, the duration of one puff. This can increase compatibility of an electronic cigarette to various types of heating elements, and/or may compensate for dropping output voltage of the power source.

For conventional electronic cigarettes, a heating circuit typically includes a heating element connected to the power source via a switching element which is turned on when a puff is detected and is still on for a constant time of time for each puff.in contract, with the present PMU the discharging time of the power source is adjusted dynamically to obtain more consistent vaporization over the same time interval. Consequently, a more consistent amount of aerosol may be inhaled by a user during each puff.

To compensate for an output voltage of the power source which drops over the discharging time, waveform control techniques, for example, PWM (pulse width modulation) technique maybe used to control at least one switching element within the heating circuit, to control the active time of the heating circuit. A waveform generator can be used to generate the desired control waveform. The waveform generator can be a PWM waveform generator within a PWM controller or PWM module in a microcontroller, for example, a metal-oxide-semiconductor field-effect transistor "MOSFET." A high-time and low-time ratio is determined, which is then used by the PWM controller for controlling the ON/OFF switching of the heating circuit.

In designs where the resistance of the heating element changes as the working temperature changes, the instantaneous resistance of the heating element may be measured in real-time by incorporating a reference component, for example a reference resister, into the heating circuit to control the active time of the heating circuit.

Changing resistance of the heating element may change the amount of aerosol generated during the process of vaporization, resulting in variation in the amount of the resulting in variations in the amount or character of the vapor generated, the nicotine for example, need to be controlled within a particular range so that human being's throat will not be irritated or certain administrative regulatory requirements could be meet. Therefore, another benefit of the dynamic output power management technique is that it can be compatible to various types of heating elements, for example, metal coils and heating fiber among others. Especially for heating element made from fibers, carbon fiber bundles for example, of which a precise resistance cannot be feasibly maintained for all the carbon fiber bundles in a same batch, the dynamic output management technique is desirable since it can adjust the output power within a range in responsive to carbon fiber bundles with resistance within a range of, for example 1.5 ohms. This would alleviate the burden of the manufacturing process of the carbon fiber bundle and lower the cost of the carbon fiber bundles as a result.

FIG. 1 shows an example of an electronic cigarette which may have a size and shape generally comparable to a real tobacco cigarette, typically about 100 mm with a 7.5 mm diameter, although lengths may range from 70 to 150 or 180 mm, and diameters from 5 to 20 mm. A power source or battery 20 is contained within the electronic cigarette housing, which is optionally divided into a first housing 8 and a second housing 9. One or more inlets 4 are provided in the housing, and an outlet 14 is located at the back end of the electronic cigarette. An electronic controller 2 including the PMU is electrically connected to the battery and to the heating element 10, which may be in the form of a wire coil. A liquid holding container or space 15 may surround a channel 12 extending from the heating element 10 to the outlet 14.

Figure 1A:
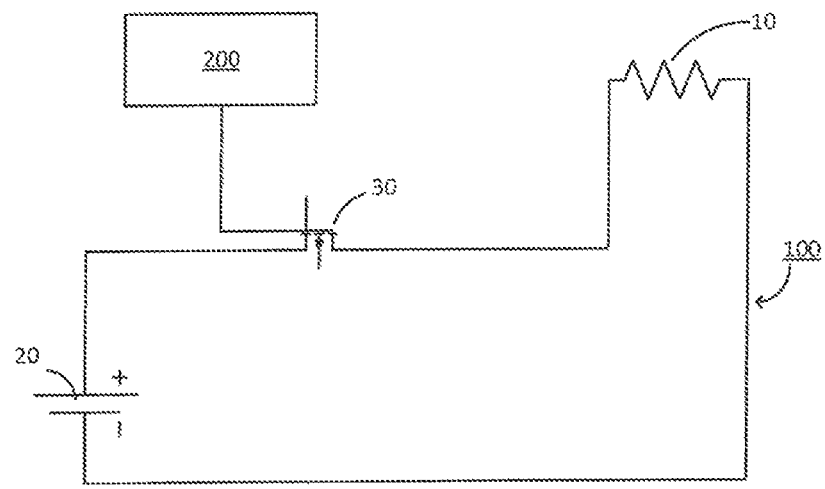
FIG. 1A is a diagram showing a heating circuit of an electronic cigarette including a dynamic output power management unit.

Referring to FIG. 1A, a heating circuit 100 includes the heating element 10, the power source 20, and a first switching element 30 connected between the heating element 10 and the power source 20. The heating element 10 can be treated or remain substantially dry during working so that it has a substantially constant resistance at the working temperature range. The first switching element 30 can be a first MOSFET switch, which is configurable between an On state and an OFF state by a first control waveform. The power source 20 can be a common battery, for example, a Nickel-Hydrogen rechargeable battery, a Lithium rechargeable battery, a Lithium-manganese disposable battery, or a zinc-manganese disposable battery. The first control waveform can be generated by a waveform generator which can be included in the power management unit 200 or can be implemented by a dedicated circuitry or by a processor or a controller implementing functions.

Figure 5:
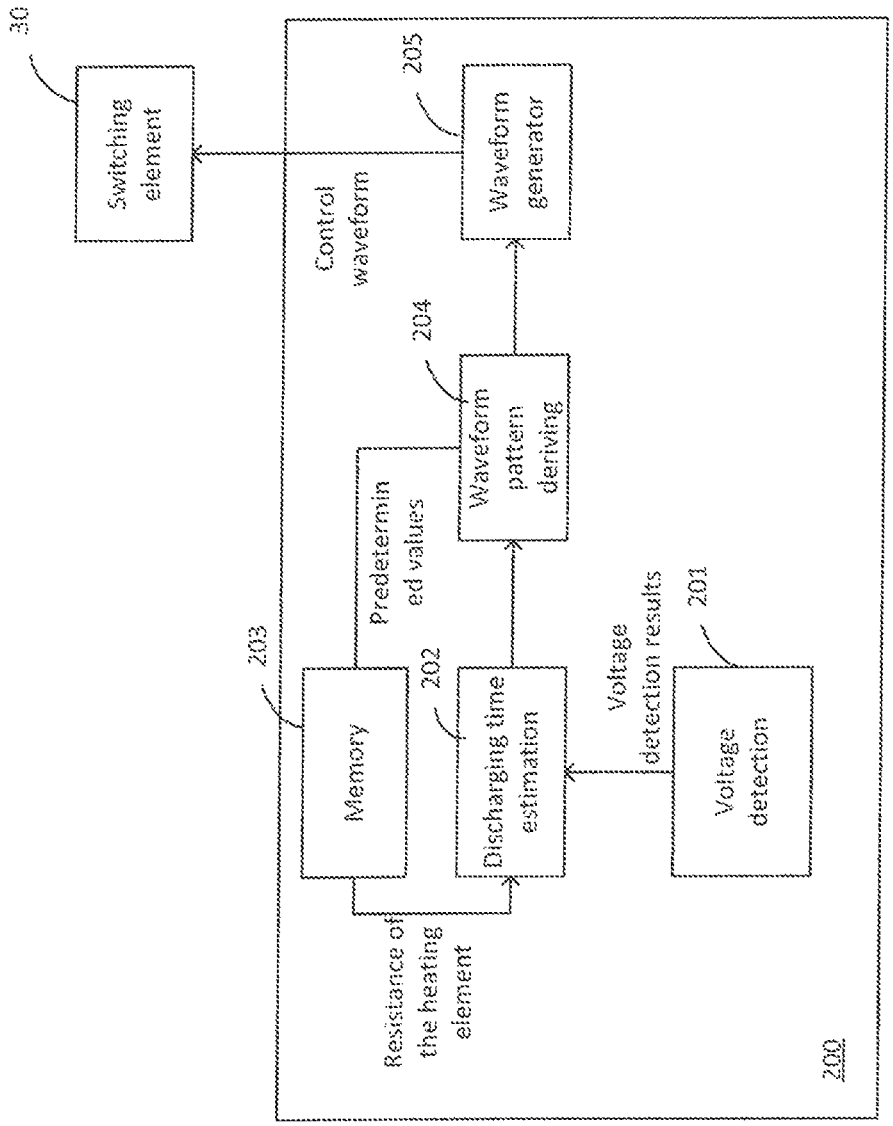
FIG. 5 is a block diagram illustrating the dynamic output power management unit in FIG. 1A.

FIG. 5 shows an alternative embodiment where the PMU 200 has at least one voltage detector 201 for detecting output voltage of the power source 20. A discharging time estimation device 202 estimates the discharging time of the power source in the duration of a puff based on the output voltage detected and a resistance of the heating element stored in a memory device 203. A waveform pattern deriving device 204 determines the high-time and low-time ratio of the first control waveform based on the estimated discharging time and a predetermined power consumption P and a time a puff normally lasts tp stored in the memory. A waveform generator 205 generates first control waveform according to the pattern determined.

Figure 7A:
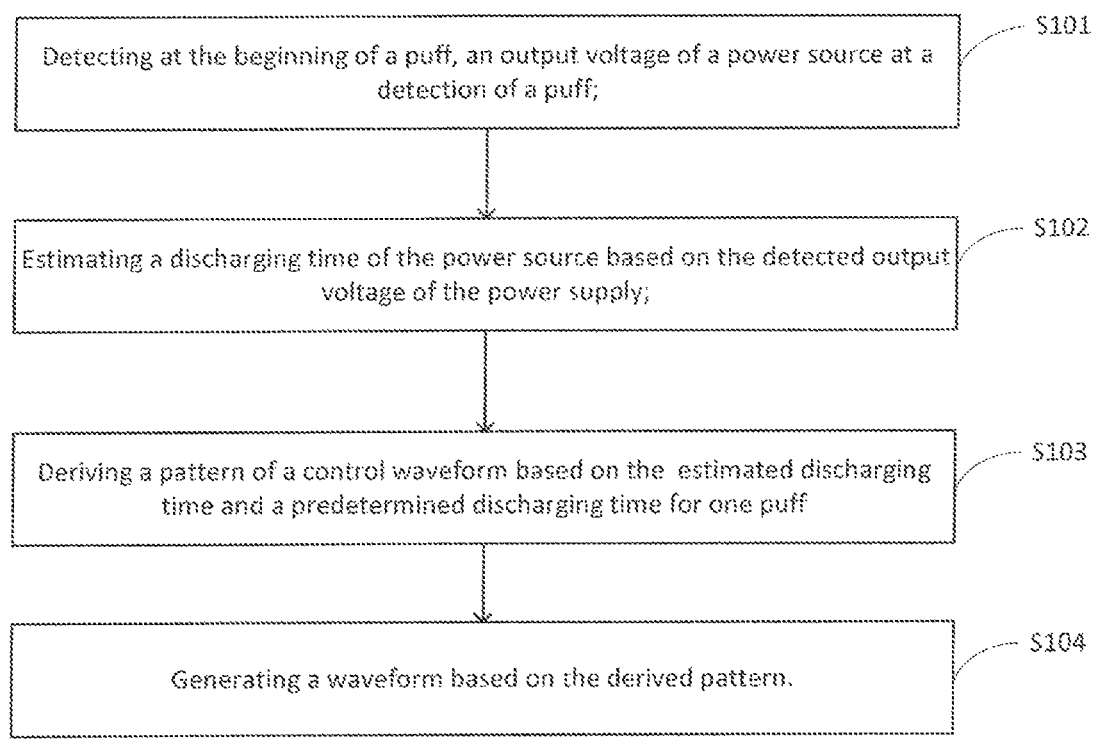
FIG. 7A is a flowchart of a control method by the power management unit illustrated in FIG. 5.

As illustrated in FIG. 7A, at step S101 detection of the working voltage of the power supply can be done at the beginning of each puff to derive the time the heating element should be powered. The predetermined power consumption P and the time a puff normally lasts tp are known parameters and can be stored in advance within the memory device 203, for example, registers within a microcontroller.

The energy consumption of the heating element for one puff is estimated based on the resistance of the heating element using Equation 1, which is then used at step S102 for deriving a period of time that needed for providing the heating element with the desired energy:

$$P \times t_p / t_{h-p} = V^2 / R_h \text{ or } t_{h-p}/t_p = P \times R_h / V^2 \qquad \text{Equation 1}$$

wherein P is a predetermined power consumption of the heating element for one puff; $t_{h-p}$ is the time of the heating element should be powered on; $t_p$ is the time a puff normally last; V is the working voltage of the power supply; and $R_h$ is the resistance of the heating element.

With the estimated time that the heating element is to be powered, at step S103 a waveform pattern can be derived.

For example, the derived $t_{h-p}$ can be equal to or greater than the duration of a puff $t_p$. In this circumstance, the first MOSFET switch 30 can be maintained at the OFF state during the entire puff duration. The output of the power source 20 that applied onto the heating element 10 in this puff then presents in the form of a DC output.

In other examples, the derived $t_{h-p}$ can be smaller than the duration of each puff $t_p$. In this case, the first MOSFET switch 30 can be configured according to different control waveforms of different high-time and low-time ratios, to reflect the ratio of $t_{h-p}$ to $t_p$.

A waveform device, for example the waveform generator 205 is then used at step S104 to generate the first control waveform according to the derived waveform pattern.

Figure 7B:
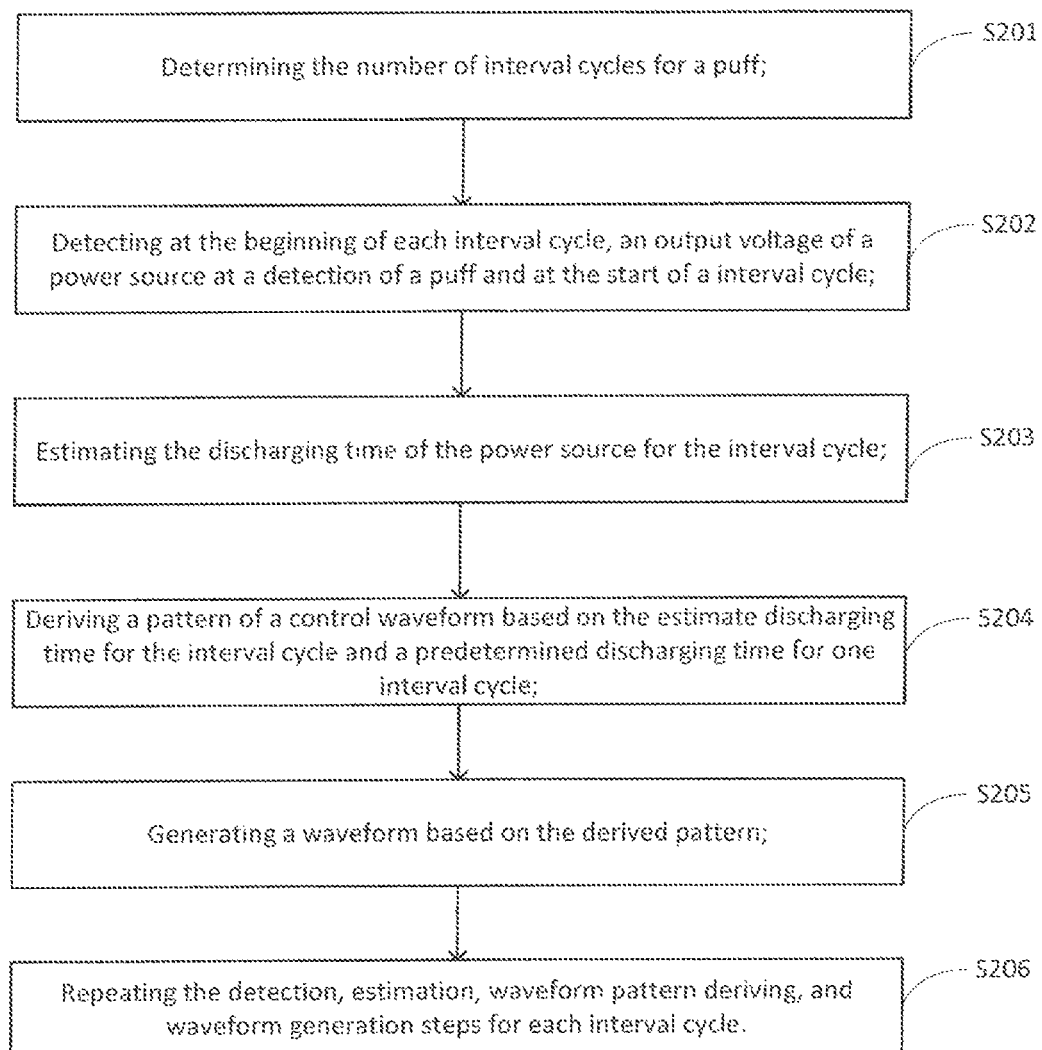
FIG. 7B is a flowchart of a control mechanism implemented by the power management unit illustrated in FIG. 5 according another embodiment of the invention.

In a further embodiment, as illustrated in FIG. 7B, a puff can be divided into multiple interval cycles, for example N interval cycles, each cycle $t_c$ will last for a time of $t_c = t_p/N$, S201. Working voltage of the power source can be slightly different in the respective interval cycles and discharging time of the power source for each interval cycle can be derived accordingly based on detection of the working voltage at the beginning of each interval cycle S202. Similar algorithms as described above can be applied to each cycle to determine the time the heating element should be powered for the duration of $t_c$. The time of the heating element should be powered for each cycle $t'_{h-p}$ can be derived at step S203 from Equation 2:

$$t'_{h-c}/t_c = P \times R_h / V^2 \qquad \text{Equation 2}$$

wherein P is a predetermined power consumption of the heating element for one interval cycle, and the predetermined power consumption for one interval cycle can be a result of the predetermined power consumption for a cycle divided by the number of interval cycles.

Similarly, with the estimated time that the heating element is to be powered at step S204, a waveform pattern can be derived.

The derived $t'_{h-p}$ can be equal to or greater than the duration of an interval cycle $t_c$. The first MOSFET switch 30 can thus be maintained at the OFF state during the entire interval cycle. The output of the power source 20 applied to the heating element 10 in this interval cycle is in the form of a DC output.

In other examples, the derived t'h-p can be smaller than the duration of each puff $t_c$, and the first MOSFET switch 30 can be configured according to different control waveforms of different high-time and low-time ratios, to reflect the ratio of $t'_{h-p}$ to $t_c$. In accordance with this step, energy converted in a period of time is substantially identical to a predetermined energy conversion value for a same period of time.

A waveform device, for example the waveform generator 205 is then used in step S205 to generate the first control waveform according to the derived waveform pattern. The process is repeated until waveforms for all interval cycles of the puff are generated. Bipolar transistors and diodes can also be used as switching elements for activating or deactivating the heating circuit instead of using MOSFET's as switching elements The first control waveform can be a PWM (Pulse Width Modulation) waveform and the waveform generator can be a PWM waveform generator. The PWM waveform generator can be part of a microprocessor or part of a PWM controller.

Figure 1B:
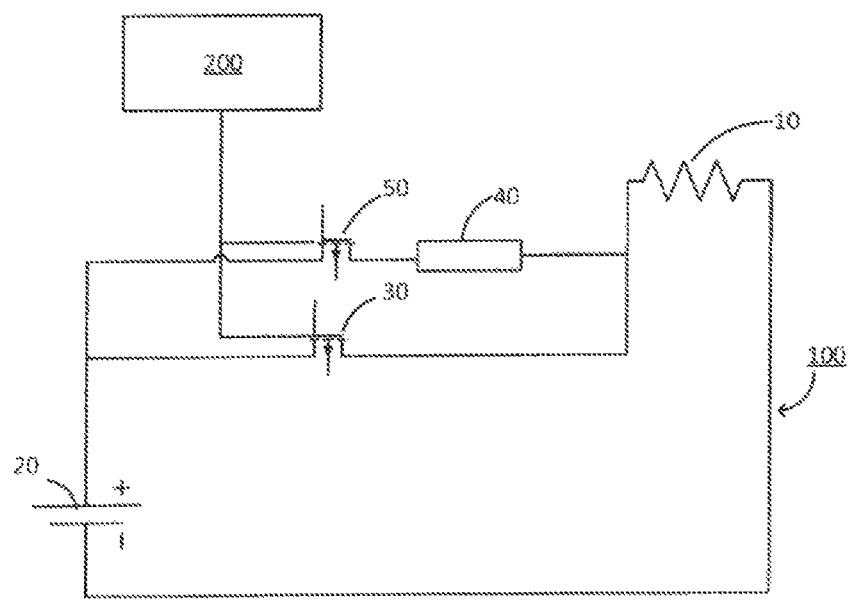
FIG. 1B is a diagram showing another embodiment of a heating circuit of an electronic cigarette including a dynamic output power management unit.

The design in FIG. 1B includes the elements of FIG. 1A and further includes a reference element 40, for example a reference resistor or a set of reference resistors connected in series or in parallel and having a substantially constant resistance value. The reference element 40 is connected in series with the heating element 10 and disconnected from the heating circuit via a second switching element 50, for example a second MOSFET switch which is configurable between an ON state and an OFF state by a second control waveform. The reference resistor 40 has a known resistance $R_f$ that is consistent over the working temperature and working time of the electronic cigarette.

Figure 6:
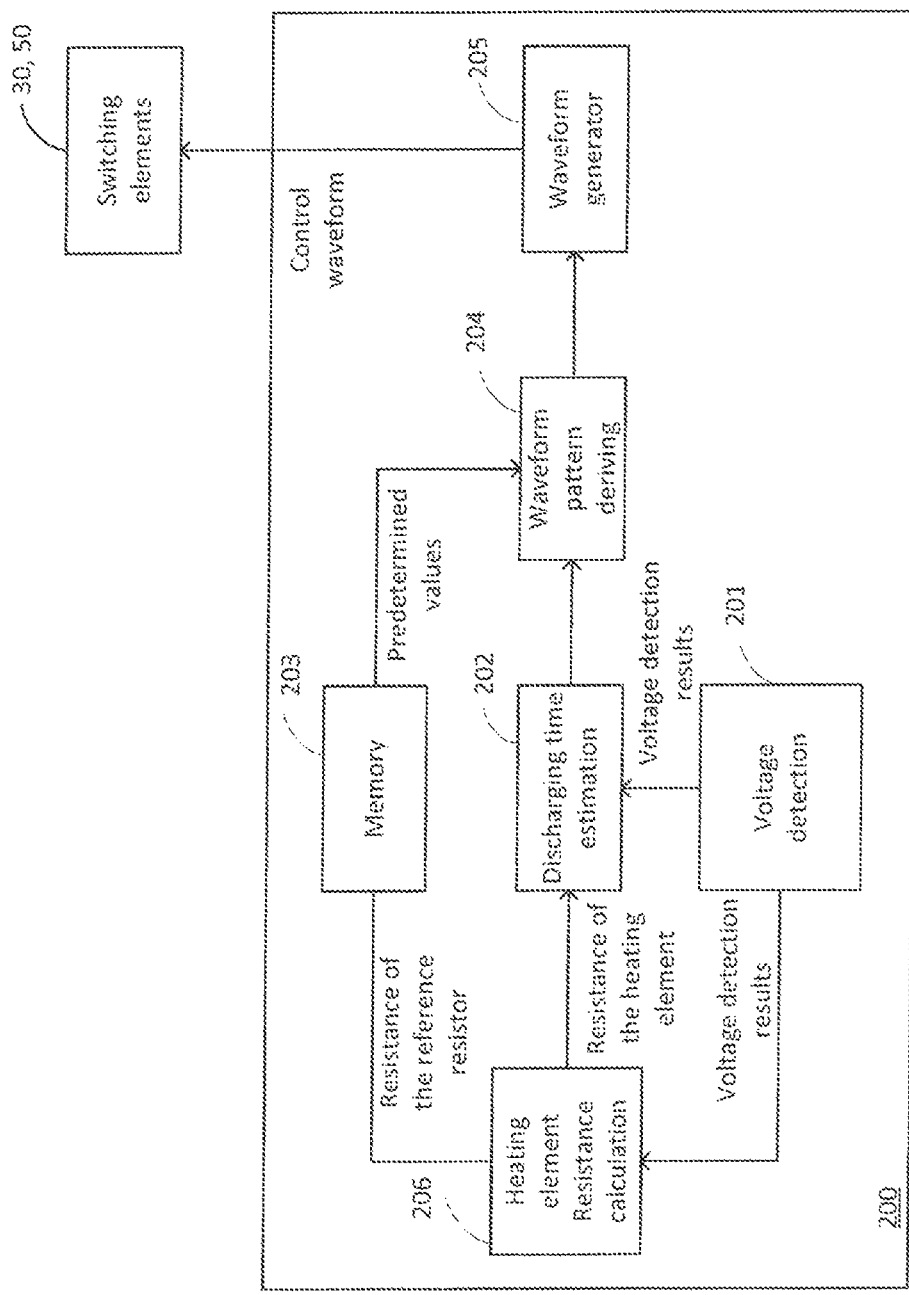
FIG. 6 is a block diagram illustrating the dynamic output power management unit in FIG. 1B.

A block diagram of the power management unit 200 of FIG. 1B is illustrated in FIG. 6. The unit 200 has at least one voltage detector 201 for detecting an output voltage of the power source 20 and/or a voltage drop across the reference resistor, and/or a voltage drop across the heating element. A heating element resistance calculation unit 206 calculates the instantaneous resistance or mean value of the resistance of the heating element based on the detected output voltage of the power source and/or the voltage drop across the reference resistor and/or the voltage drop across the heating element, and a resistance value of the reference resistor stored within a memory device 203. A discharging time estimation device 202 estimates the discharging time of the power source in the duration of a puff based on the output voltage detected and the calculated resistance of the heating element. A waveform pattern deriving device 204 determines the different high-time and low-time ratio of the first control waveform based on the estimated discharging time and a predetermined power consumption P and a time a puff normally lasts $t_p$ stored in the memory device 203. A waveform generator 205 generates the first control waveform according to the pattern determined.

Figure 8A:
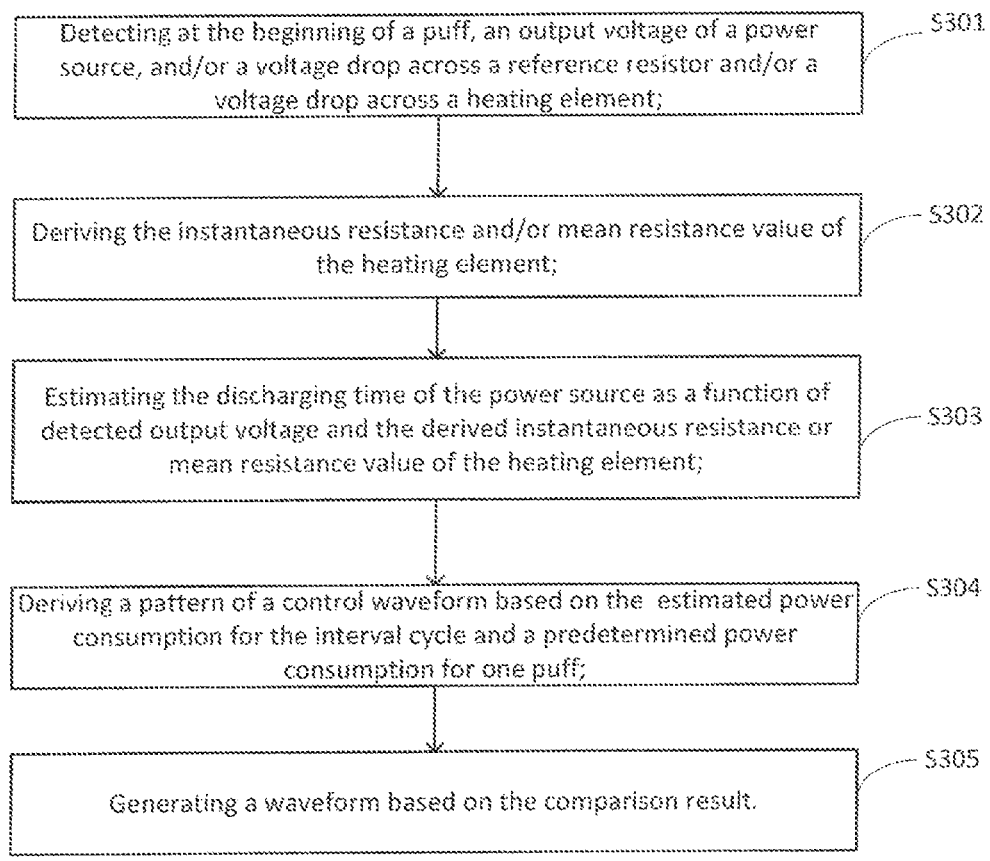
FIG. 8A is a flowchart of an alternative control method by the power management unit illustrated in FIG. 6.

To detect an output voltage of a power source, and/or a voltage drop across a reference resistor and/or a voltage drop across a heating element 10, the first MOSFET switch 30 is configured to the ON state and the second MOSFET switch 50 is configured to the OFF state. The power source 20, the reference resistor 40 and the heating element 10 are connected as a closed circuit. As illustrated in FIG. 8A, at step S301 detection of the working voltage of the power source 20 and/or the voltage drop across the heating element 10 are performed. The instantaneous resistance can then be derived at step S302 by calculating with reference to the resistance of the reference resistor 40 and the voltages measured using Equation 3.

$$R_h = V_2 \times R_f / (V_1 - V_2) \qquad \text{Equation 3}$$

wherein $R_h$ is the instantaneous resistance of the heating element; $R_f$ is the resistance of the reference resistor; $V_1$ is the working voltage of the DC power source; and $V_2$ is the voltage drop across the heating element.

Alternatively or in addition, at step S302 voltage drop across the reference resistor 40 can be detected for deriving the instantaneous resistance of the heating element 10. Equation 3 can in turn be slightly adjusted to involve the voltage drop of the reference resistor 40 instead of the output voltage of the power source 20.

The measurement and calculation of the instantaneous resistance of the heating element can be repeated, and a mean value of can be derived from the result of the repeated calculation results and can be used for further processing.

After the instantaneous resistance or the mean resistance of the heating element is calculated. An output voltage of the power source 20 is detected again with the first MOSFET switch in the OFF state and the second MOSFET switch in the ON state. A discharging time of the power source for one puff is then estimated at step S303 based on the calculated resistance of the heating element and the newly detected output voltage of the power source using Equation 1. After the discharging time is estimated, at step S304 a waveform pattern can be determined and control waveforms can be generated at step S305.

Figure 8B:
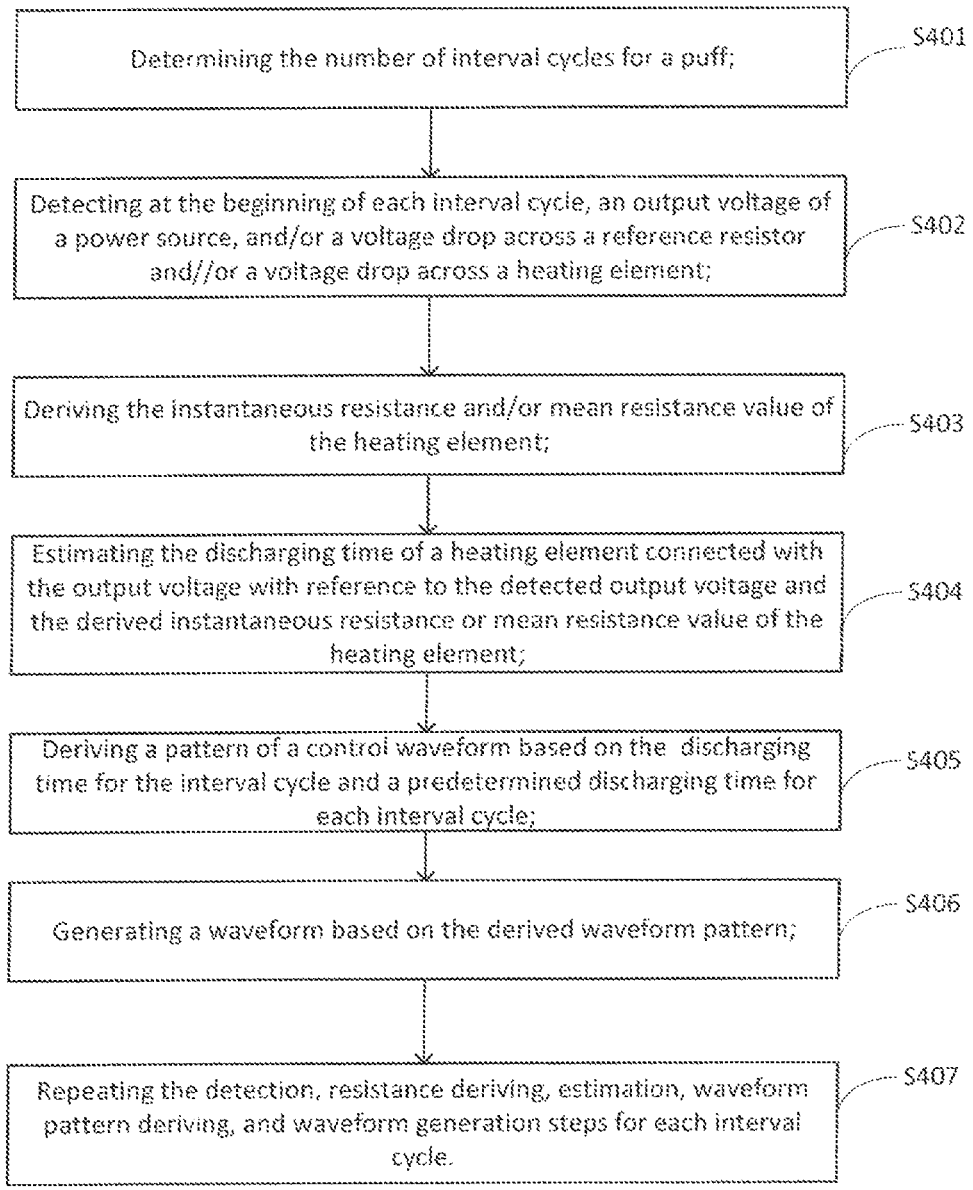
FIG. 8B is a flowchart of an alternative control method by the power management unit illustrated in FIG. 6.

Likewise, in this embodiment, as illustrated in FIG. 8B, a puff can also be divided into multiple interval cycles, for example N interval cycles, each cycle $t_c$ lasting for a time of $t_c = t_p/N$, S401. Equation 2 can again be used to derive the time of the heating element that should be powered for each cycle.

At a beginning of a first time interval, the first MOSFET switch 30 is ON and the second MOSFET switch 50 is OFF. Voltage drop across the reference resistor 40 and the output voltage of the power source are then detected at step S402. The instantaneous resistance of the heating element 10 can then be derived from Equation 3 at step S403.

After the instantaneous resistance of the heating element is derived, the first MOSFET switch 30 is configured to the OFF state and the second MOSFET switch 50 is configured to the ON state whereby the reference resistor 40 is disconnected from the heating circuit 100. The output voltage V of the power source 20 is then detected again and the discharging time of the power source 20, that is, the time that the first MOSFET switch 30 needs to be maintained at the OFF state in the interval cycle for a desired energy conversion at the heating element, is derived according to Equation 2 at step S404.

The time that the first MOSFET switch 30 should be maintained at the OFF state is then derived for each interval cycle following the same process as mentioned above. In some embodiments, the instantaneous resistance of the heating element is derived at the beginning of each puff and is only derived once and is then used for deriving the time that the first MOSFET switch 30 should be at the OFF state for the duration of the puff. In other embodiments, the instantaneous resistance of the heating element 10 is derived at the beginning of each interval cycle and is used only for deriving the time that the first MOSFET switch 30 needs to be maintained at the OFF state for that interval cycle. Deriving the instantaneous resistance of the heating element may be desirable if the heating element is very sensitive to its working temperature.

Similarly, a mean value of the resistance for the reference resistor can be derived instead and used for deriving the time that the first MOSFET switch needs to be configured at the OFF state.

In some embodiments, the derived $t'_{h-p}$ can be equal to or greater than the duration of each interval cycle $t_c$. In this case, the first MOSFET switch 30 will be maintained at the OFF state during the entire interval cycle and based on the ratio of $t'_{h-p}$ to $t_c$, the first MOSFET switch 30 may also be maintained at the OFF state for a certain period of time in a subsequent interval cycle or the entire duration of the subsequent interval cycle. The power source 20 supplies a DC output current to the heating element 10 in this interval cycle or interval cycles.

In other embodiments, the derived $t'_{h-p}$ can be smaller than the duration of each interval cycle $t_c$. Then, the first MOSFET switch 30 is configured according to different control waveforms, for example PWM waveforms of different high time and low time ratios, to reflect the ratio of $t'_{h-p}$ to $t_c$.

For example, at step S405 a waveform pattern is then determined according to the ratio of $t'_{h-p}$ to $t_c$ and the first and the second control waveforms are generated according to the determined waveform pattern at step S406. Control waveforms for all interval cycles are generated by repeating the above steps at step S407. Similar to the first control waveform, the second control waveform can also be a PWM waveform and the waveform generator can be a PWM waveform generator. The PWM waveform generator can also be part of a microprocessor or part of a PWM controller.

Alternatively or in addition to the embodiment described in FIG. 1B, the reference resistor 40 can be arranged in parallel with the heating element 10. In this arrangement, the instantaneous resistance of the heating element 10 can be derived with reference to the current flow across each branch of the heating circuit. In some embodiments, the voltage across the reference resistor 40 and the heating element 10 can be detected by a voltage probe, a voltage measurement circuit, or a voltage measurement device.

Calculations according to Equations 1 to 3 can be performed by a processor or a controller executing instruction codes or by dedicated calculation circuits designed to perform the above mentioned logic. A microprocessor having a PWM function and a storage function may be used. The storage function can store the instructions code that when executed by the microprocessor can implement the logic as described above.

In a further embodiment, instead of deriving the discharging time to generate the control waveforms, an estimated power consumption of the heating element can be derived for generating the control waveforms.

Figure 9:
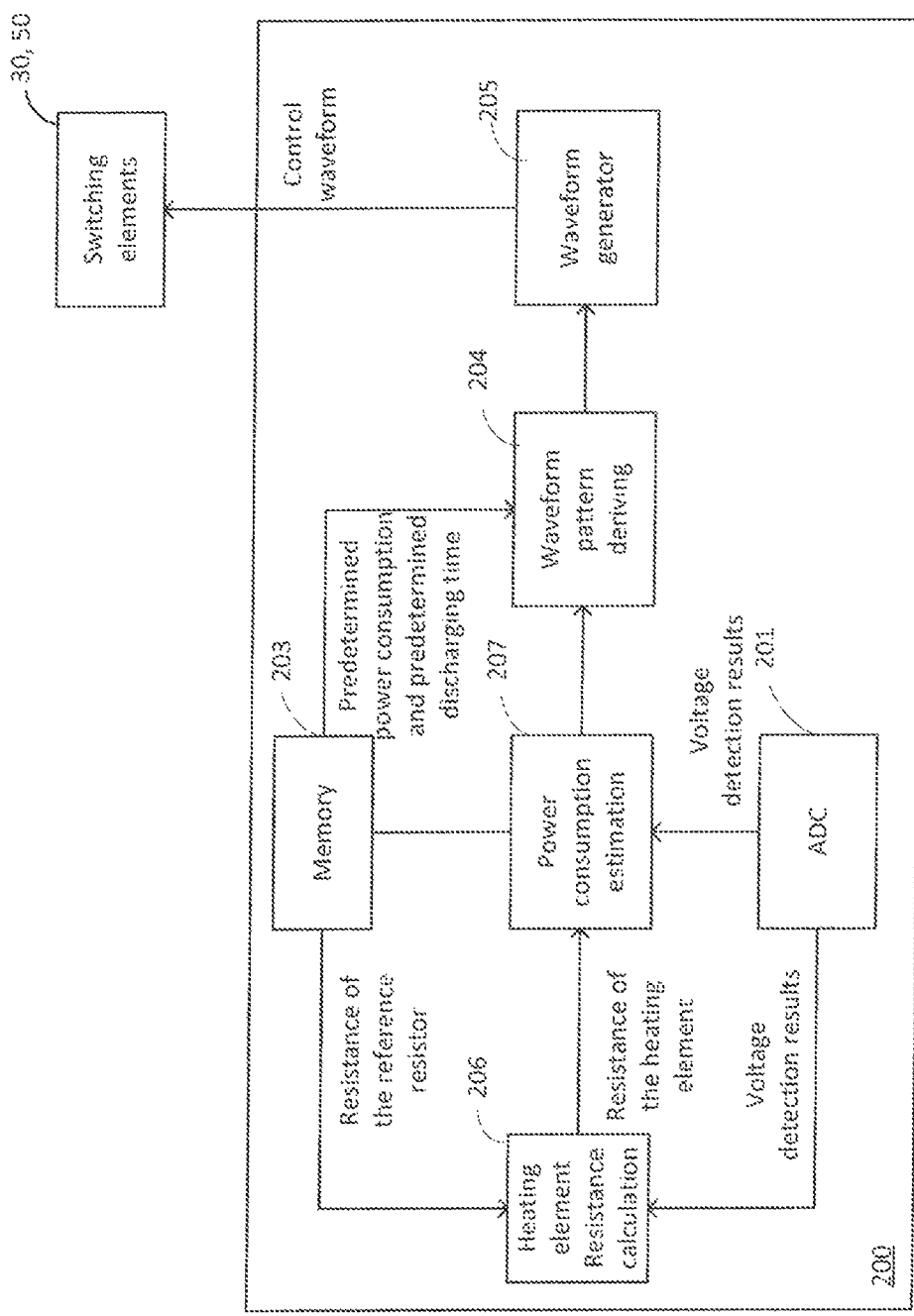
FIG. 9 is a block diagram illustrating another example of the dynamic output power management unit in FIG. 1B.

As illustrated in FIG. 9, the power management unit in this example includes an ADC 201 for detecting a first output voltage of the power source 20 and/or a voltage drop across the reference resistor 40, and/or a voltage drop across the heating element 10. A heating element resistance calculation unit 206 calculates the instantaneous resistance or mean value of the resistance of the heating element based on the detected first output voltage of the power source and/or the voltage drop across the reference resistor and/or the voltage drop across the heating element. A resistance value of the reference resistor 40 stored within a memory device 203. A power consumption estimation device 207 estimates the power consumption during a given period of time, for example the duration of a puff or an interval cycle within the puff, based on a second output voltage detected and the calculated resistance of the heating element. A waveform pattern deriving device 204 determines the hightime and lowtime ratio of the first control waveform based on the estimated power consumption and a predetermined power consumption P stored in the memory device 203. A waveform generator 205 generates a first control waveform according to the pattern determined.

The heating element in this example may be a carbon fiber based heating element. An ADC of a microcontroller reads the voltage ratio of the carbon fiber heating element $V_{Wick}$ and the voltage drop $V_{res}$ across a reference resistor having a resistance of $R_{standard}$. The resistance of the standard resistor is known, and the resistance of the carbon fiber heating element can be derived.

The reference resistor is then disconnected from the heating circuit and the carbon fiber heating element. The ADC then reads the closed circuit voltage of the carbon fiber $V_{close}$. The power of the carbon fiber can be calculated by Equation 4:

$$P_{CF} = V_{close}^2 / R_{wick} \quad \text{Equation 4}$$

The estimated power PCF can be for example 3.2 W which is higher than a predetermined value of 2.5 W, the ON and OFF time of the first MOSFET switch 30 can then be determined by determining the high-time and low-time ratio of the control waveform.

For example, in every 50 ms long cycles, the hightime is 50 ms*hightime/lowtime=50 ms*0.78=39 ms, the lowtime is 50 ms−hightime=11 ms.

A control waveform is then generated by the waveform generator to configure the ON/OFF time of the first MOSFET switch 30.

In case the estimated PCF is smaller than the predetermined value of 2.5 W, the output waveform to the first MOSFET controller will be all OFF, and the output of the power source will be provided as DC.

Figure 2:
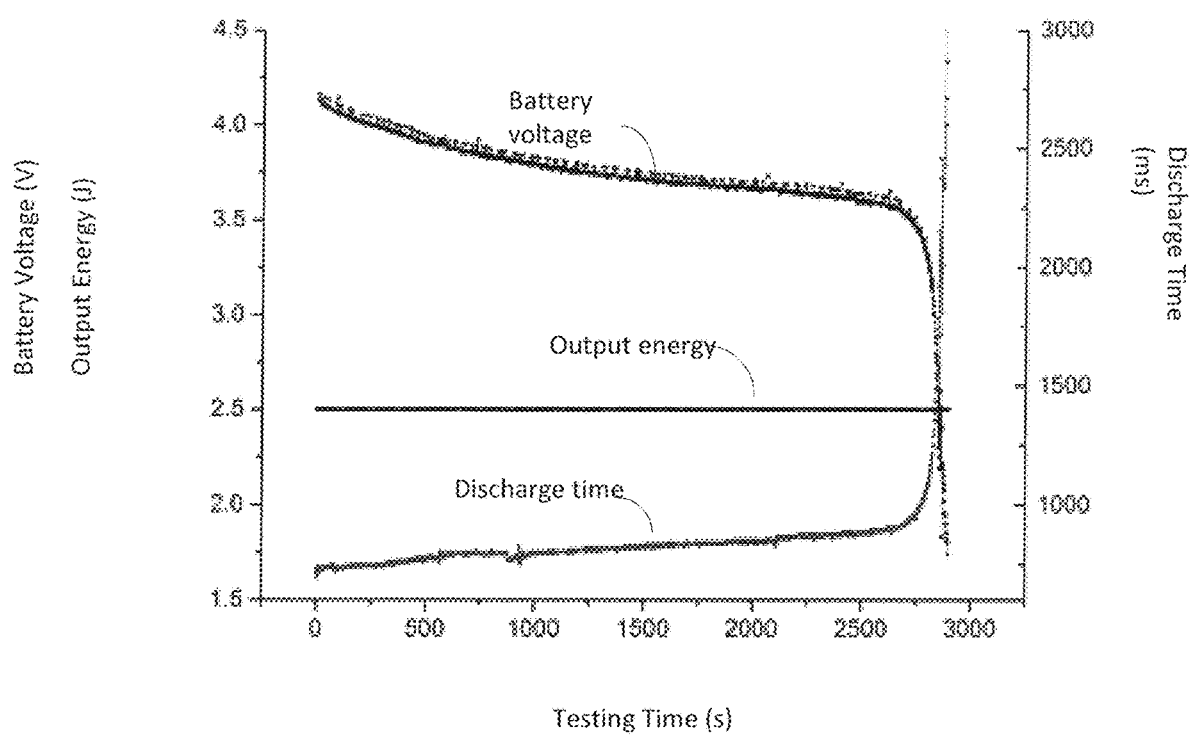
FIG. 2 is a diagram showing the discharging time of a power supply when the heating element has a constant resistance.
Figure 3:
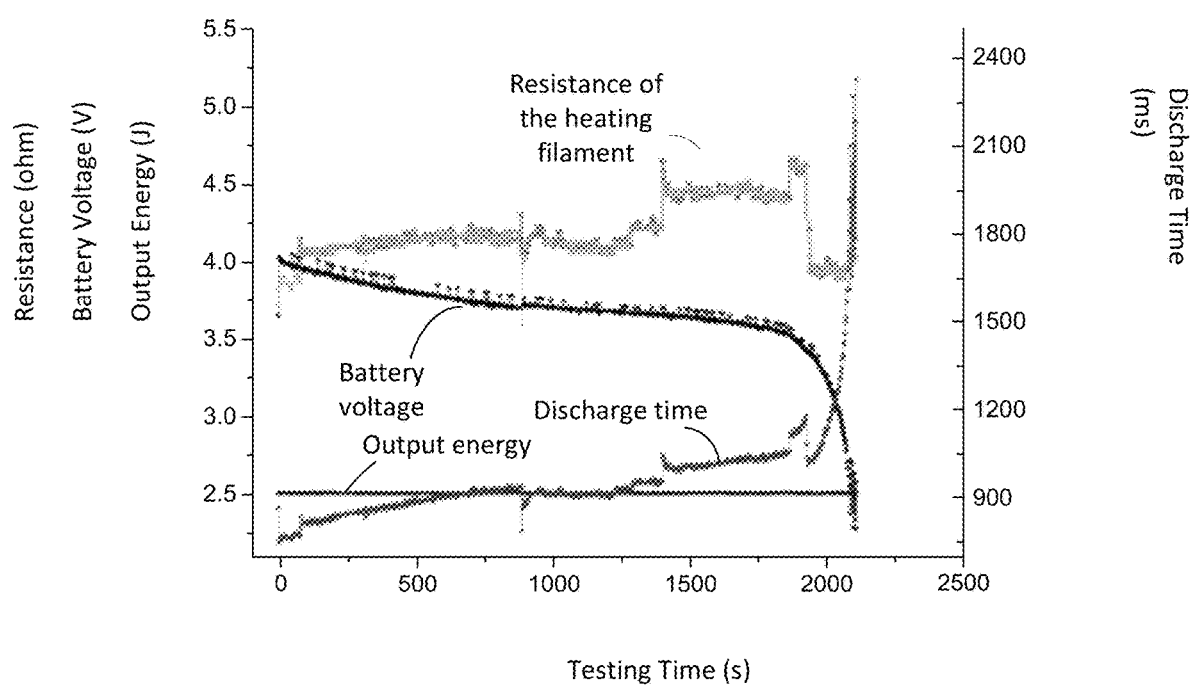
FIG. 3 is a diagram showing the discharging time of a power supply when the heating element has a variable resistance.
Figure 4:
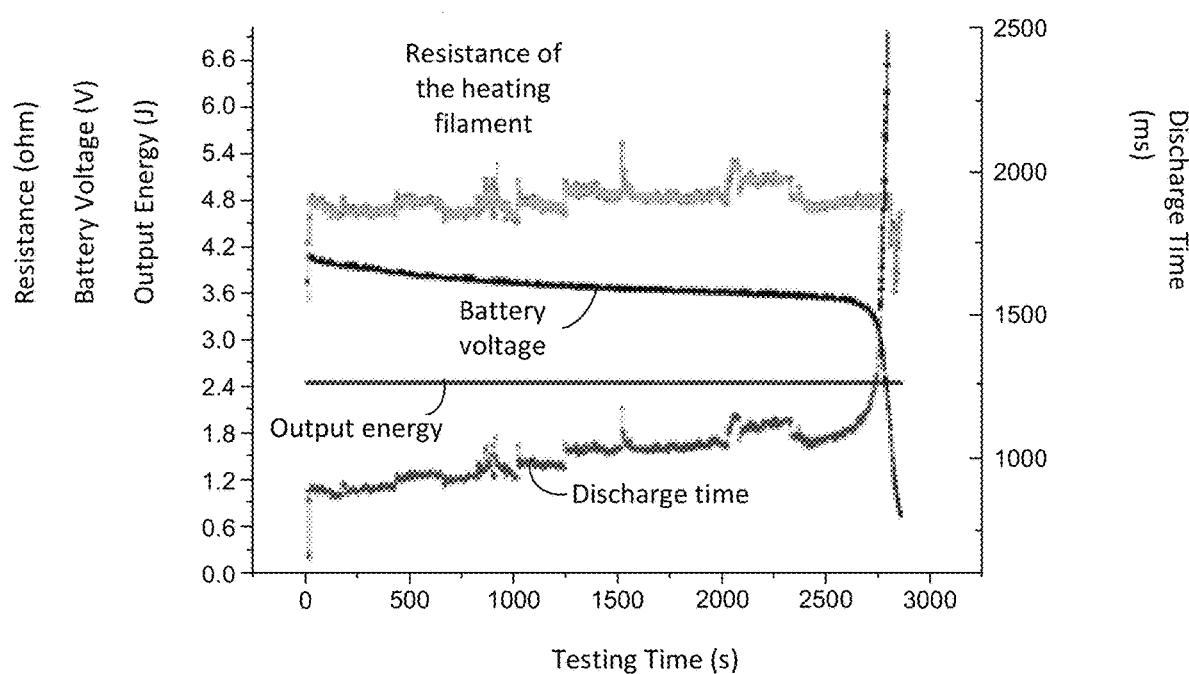
FIG. 4 is a diagram showing the discharging time of another power supply when the heating element has a variable resistance.

FIGS. 2 to 4 are diagrams showing testing results of the heating circuit using the power management unit. These results show substantially constant output have been maintained even though the resistance of the heating element may vary during the working cycle of the heating element and/or the battery voltage may drop with the lapse of time.

Testing Result 1: Substantially Constant Resistance of the Heating Element with Decreasing Battery Capacity In one example, dynamic discharging tests using the dynamic output power management unit of FIG. 1A were carried out on a dry heating element, i.e., a heating element having substantially consistent resistance. The results are shown in FIG. 2, wherein the data lines from the top to the bottom represent the battery voltage V, the output energy in J at 280 mAh, and the discharge time in ms, i.e. the powered time, over testing time in seconds.

In some examples, the resistance of the heating element changes depending on the working condition of the heating element, e.g. amount of e-solution the heating element contacts, carbonization around/in the heating element, and the working temperature. The heating element may be a conventional heating element or a fiber based heating element, for example a carbon fiber heating element.

Example 2

Wetted Heating Element With Decreasing Battery Capacity

In another example, wet dynamic discharging tests using the dynamic output power management unit of FIG. 1A or 1B were carried out on a wetted heating element, i.e., the resistance of the heating element may change when it has different amount of liquid. The results are shown in FIG. 3. The data lines from the top to the bottom represent the resistance of the heating element in ohms, the battery voltage V, the output energy in J, at 240 mAh, and the discharge time in ms, i.e. the powered time, over testing time in seconds.

Example 3

Wetted Heating Element with Decreasing Battery Capacity

The results for another set of wet dynamic discharging tests are shown in FIG. 4. The data lines from the top to the bottom represent the resistance of the heating element in ohms, the battery voltage V, the output energy in J at 280 mAh, and the discharge time in ms, i.e. the powered time, over testing time in seconds.

The power management system described may include dynamic output power management unit for a heating circuit of an electronic smoking device, with the PMU having at least one voltage detection device to detect an output voltage of a power source, and/or a voltage drop across a heating element operable to be connected to or disconnected from the power source via a first switching element, and/or a voltage drop across a reference element operable to be connected to or disconnected from the heating circuit via a change of state of a second switching element from a first state to a second state and from a second state to the first state. A controller is configured to change the second switching element from the first state to the second state; to receive a first detection result from the detection device; derive a resistance of the heating element; change the second switching element from the second state to the first state; receive a second detection result from the voltage detection device; and derive a discharging time of the power source as a function of the resistance of the heating element and the second voltage detection. As a result, energy converted in a period of time is substantially identical to a predetermined energy conversion value for a same period of time.

The power management system described may operate on instructions stored on non-transitory machine-readable media, the instructions when executed causing a processor to control a voltage detection device to detect a first output voltage of a power source, and/or a voltage drop across a heating element operably connected to the power source via a first switching element, and/or a voltage drop across a reference element operably connected to the power source via a second switching element. The first output voltage is detected when the reference element is connected to the power source. The instructions may direct the processor to derive a resistance of the heating element as a function of the at least two of the first output voltage of a power source, the voltage drop across the heating element, and to control the voltage detection device to detect a second output voltage of the power source. The processor may then estimate the discharging time of the power source for the puff as a function of the second output voltage of the power source and the derived resistance of the heating element such that an energy converted in the puff is substantially identical to a predetermined energy conversion value for one puff.

The invention claimed is:

1. A method of operating an electronic smoking device, comprising,
   detecting an output voltage of a power source of a heating circuit in the electronic smoking device;
   estimating a discharging time of the power source during a puff based on the output voltage of the power source; and
   providing electrical energy from the power source to a heating element during the puff equivalent to a predetermined energy conversion value for one puff.

2. The method of claim 1 further comprising deriving a pattern of a waveform based on the estimated discharging time; generating a control waveform based on the derived pattern; and using the control waveform to control the electrical energy provided by the power source.

3. The method of claim 2 further comprising dividing the puff into multiple interval cycles; detecting the output voltage at the beginning of each interval cycle; and estimating a discharging time of the power source for each interval cycle.

4. The method of claim 2 further comprising repeating the detecting, estimating and waveform generating steps for each puff.

5. The method of claim 2 wherein the discharging time is estimated based on the output voltage of the power source and a resistance of a heating element.

6. A method of operating an electronic smoking device, comprising,
   A) detecting a value for one or more of:
      i) a first output voltage of a power source;
      ii) a voltage drop across a heating element;
      iii) a voltage drop across a reference resistor;
   B) deriving an instantaneous or mean value of a resistance of the heating element based on the one or more values detected in step A;
   C) estimating a discharging time of the power source for a puff as a function of the one or more values detected in step A and the derived resistance of the heating element; and
   D) providing an amount of electrical energy to the heating element during the puff that is equivalent to a predetermined value for one puff.

7. The method of claim 6 wherein a first output voltage of the power source is detected at the beginning of each puff.

8. The method of claim 7 further comprising deriving a pattern of a control waveform based on the estimated discharging time and a predetermined discharging time for each puff; and generating a control waveform based on the derived pattern.

9. The method of claim 6 wherein a voltage drop across a reference resistor is detected in step A, and the first output voltage is detected when the reference resistor is connected to the power source.

10. The method of claim 6 wherein an instantaneous resistance of the heating element is derived in step B.

11. The method of claim 6 further including estimating power consumption of the heating element during a puff or during an interval cycle based on a second output voltage detected and the derived resistance of the heating element.

12. A method for power management for a heating circuit of an electronic smoking device, comprising,
   A) dividing a duration of a puff into a number of interval cycles;
   B) determining, in each interval cycle, a value of a first output voltage of a power source, and/or a voltage drop across a heating element operably connected to the power source, and/or a voltage drop across a reference resistor;
   C) deriving a resistance of the heating element as a function of any value or values determined in step B; and
   D) estimating a discharging time of the power source for the interval cycle as a function of the derived resistance of the heating element such that an amount of energy converted in the interval cycle is substantially identical to a predetermined energy conversion value for one interval cycle.

13. The method of claim 12 wherein a first output voltage of the power source is detected at the beginning of each interval cycle.

14. The method of claim 12 further comprising
   deriving a pattern of a control waveform based on the estimated discharging time and a predetermined discharging time for each interval cycle; and
   generating a control waveform based on the derived pattern.

* * * * *